United States Patent
Leidl

(10) Patent No.: US 6,186,005 B1
(45) Date of Patent: Feb. 13, 2001

(54) SURFACE WAVE LIQUID SENSOR

(75) Inventor: Anton Leidl, München (DE)

(73) Assignee: Fraunhofer-Gesellschaft Zur Forderung der Angewandten Forschung, E.V., Munich (DE)

( * ) Notice: Under 35 U.S.C. 154(b), the term of this patent shall be extended for 0 days.

(21) Appl. No.: 09/194,070

(22) PCT Filed: Jul. 10, 1997

(86) PCT No.: PCT/EP97/03667

§ 371 Date: Nov. 19, 1998

§ 102(e) Date: Nov. 19, 1998

(87) PCT Pub. No.: WO98/05953

PCT Pub. Date: Feb. 12, 1998

(30) Foreign Application Priority Data

Jul. 31, 1996 (DE) .............................................. 196 30 890

(51) Int. Cl.$^7$ .............................. G01H 5/00; G01F 23/00; H01L 41/04
(52) U.S. Cl. ........................ 73/597; 73/292; 310/313 A; 310/313 B
(58) Field of Search ..................................... 333/193, 143, 333/151; 310/313 R, 313 B, 313 A, 320; 73/292, 32 A, 54.41, 61.41, 64.55, 597 R

(56) References Cited

U.S. PATENT DOCUMENTS

| | | | |
|---|---|---|---|
| 3,803,520 | * 4/1974 | Bristol et al. | ........................ 333/154 |
| 4,602,183 | * 7/1986 | Okamoto et al. | .................... 310/313 |
| 4,726,225 | * 2/1988 | Brace et al. | ........................... 73/204 |
| 5,448,125 | * 9/1995 | Chu | .................................. 310/313 A |
| 5,682,126 | * 10/1997 | Plesski et al. | ....................... 333/193 |
| 5,694,095 | * 12/1997 | Mineyoshi | ........................... 333/193 |

FOREIGN PATENT DOCUMENTS

| | | | |
|---|---|---|---|
| 2802946 | 8/1978 | (DE) | ............................... H03H/9/00 |
| 4126335 | 2/1993 | (DE) | ............................. H03H/9/145 |
| 2070772A | 9/1981 | (GB) | ............................. G01N/25/66 |

OTHER PUBLICATIONS

Drobe, et al., Acoustic Sensors Based on Surface–Localized HPSWs for Measurements in Liquids, Elsevier Sequoia, (1993).

Benes et al., Piezoelektrische Resonatoren als Sensorelemente, e & i, (1995).

Mackerras, High–Frequency Operation of Surface–Acoustic–Wave Multielectrode Transducers, Electronic Letters, (1974).

* cited by examiner

Primary Examiner—Eric S. McCall
Assistant Examiner—Abdullahi Aw-Musse
(74) Attorney, Agent, or Firm—Michael A. Glenn

(57) ABSTRACT

A liquid sensor has comb-shaped electrodes, applied to a piezoelectric substrate, as interdigital transducers for generating an electroacoustic wave from a transmitting transducer to a receiving transducer. The number of finger pairs of the interdigital transducers and the material out of which the electrodes are made are so chosen that a surface shear wave generated by the transmitting transducer and a bulk shear wave generated by the transmitting transducer have different frequencies.

8 Claims, 1 Drawing Sheet

SURFACE WAVE LIQUID SENSOR

BACKGROUND OF THE INVENTION

1. Field of the Invention

The present invention relates to a liquid sensor and in particular to a liquid sensor which is composed of a surface-wave component.

2. Description of Prior Art

Surface-wave components have been used for decades in electronics, e.g. as bandpass filters for the high-frequency region, and manufactured in large quantities. Depending on the choice of material used for the substrate, different wave-forms are excited. For example, for gas sensor applications, Rayleigh-wave components with a deflection perpendicular to the surface are normally used. Such components, provided with a selective layer, are employed as bio/chemosensors.

If surface-wave components are to be used as sensors for the measurement of physical liquid properties, e.g. the density, the viscosity, the shear rigidity, the conductivity, the dielectric constant, etc., Rayleigh-wave modes lead to the generation of compression waves and thus to a high energy loss. For liquid sensors, components which generate purely shear waves are used. This type of wave can be excited in various piezoelectric materials, among others in all y-rotated quartz crystal cuts.

In the y-rotated quartz crystal cuts, surface shear waves (SSWs) and bulk shear waves, in particular the so-called 'surface skimming bulk waves' (SSBWs), can, however, also be excited. Surface-wave components for which these wave types can be excited are commercially available, e.g. as bandpass filters in the high-frequency region, sometimes above 1 GHZ.

When surface-shear-wave components of this type are used as sensors for the measurement of liquid properties, problems arise that play no part or only a minor part when they are used as filters. The gravest of these problems arises from the simultaneous excitation of surface shear waves (SSWs) and bulk shear waves (SSBWs) and the interference of these waves. Another problem, that can lead to considerable disturbances in the measurement effect, is the so-called 'triple transit echo'. These effects, which will be explained in more detail in the subsequent description of the present patent application, give rise to problems which render these known components unsuitable for liquid sensor applications.

Surface-wave sensors of the above type are described in H. Drobe, A. Leidl, M. Rost, I. Ruge, "Acoustic sensors based on surface-localized HPSWs for measurements in liquids", in: Sensors and Actuators A, 37–38 (1993), pp. 141–148. Piezoelectric resonators on the basis of surface waves are also known from E. Benes, M. Gröschl, "Piezoelektrische Resonatoren als Sensorelemente", in: e & i, 112. Jahrgang 1995, Heft 9, S. 471 bis 483.

SUMMARY OF THE INVENTION

It is the object of the present invention to provide surface-wave sensors for measurements in liquids which exhibit a high sensitivity to liquid properties and small design-induced disturbances.

This object is achieved by a liquid sensor consisting of comb-shaped electrodes, applied to a piezoelectric substrate, as interdigital transducers for generating an electroacoustic wave from a transmitting transducer to a receiving transducer, where the transmitting transducer generates a surface shear wave and a bulk shear wave, where the number of finger pairs of the interdigital transducers and the material out of which the electrodes are made are so chosen that a surface shear wave generated by the transmitting transducer and a bulk shear wave generated by the transmitting transducer have different frequencies.

The material chosen for the electrodes preferably has a small acoustic propagation speed. In addition, a material with a high mass per unit area is preferably used for the electrodes. The surface-wave liquid sensor is preferably so constructed that two fingers of an electrode are arranged next to one another in each case and form a pair, a pair of one electrode forming a finger quartet with a neighbouring pair of the second electrode. The number of finger quartets is preferably chosen to be greater than twice the ratio of the excitation frequency to the frequency difference between the surface shear wave and the bulk shear wave.

To reduce the disturbances created by the so-called 'triple transit echo', the insertion loss of an electroacoustic wave between the transmitting transducer and the receiving transducer is set to a loss between 10 and 30 dB, preferably between 15 and 25 dB.

In the surface-wave sensor according to the present invention, interference between the surface shear wave, which constitutes the actual useful signal, and bulk shear waves, e.g. the 'surface skimming bulk waves', is prevented. By a suitable choice of the insertion loss, the influence of the so-called 'triple transit echo' and an electromagnetic crosstalk between transmitting transducer and receiving transducer can also be reduced considerably. At the same time, the sensor according to the present invention provides increased measurement sensitivity to the viscosity of liquids. Disturbances in the measurement effect are thereby greatly reduced.

Further developments of the present invention are disclosed in the dependent claims.

BRIEF DESCRIPTION OF THE DRAWING

Preferred embodiments of the present invention will be described in more detail below making reference to the enclosed drawing, in which The single FIGURE shows the schematic diagram of a surface-wave component according to the present invention.

DESCRIPTION OF PREFERRED EMBODIMENTS OF THE INVENTION

Figure 1:
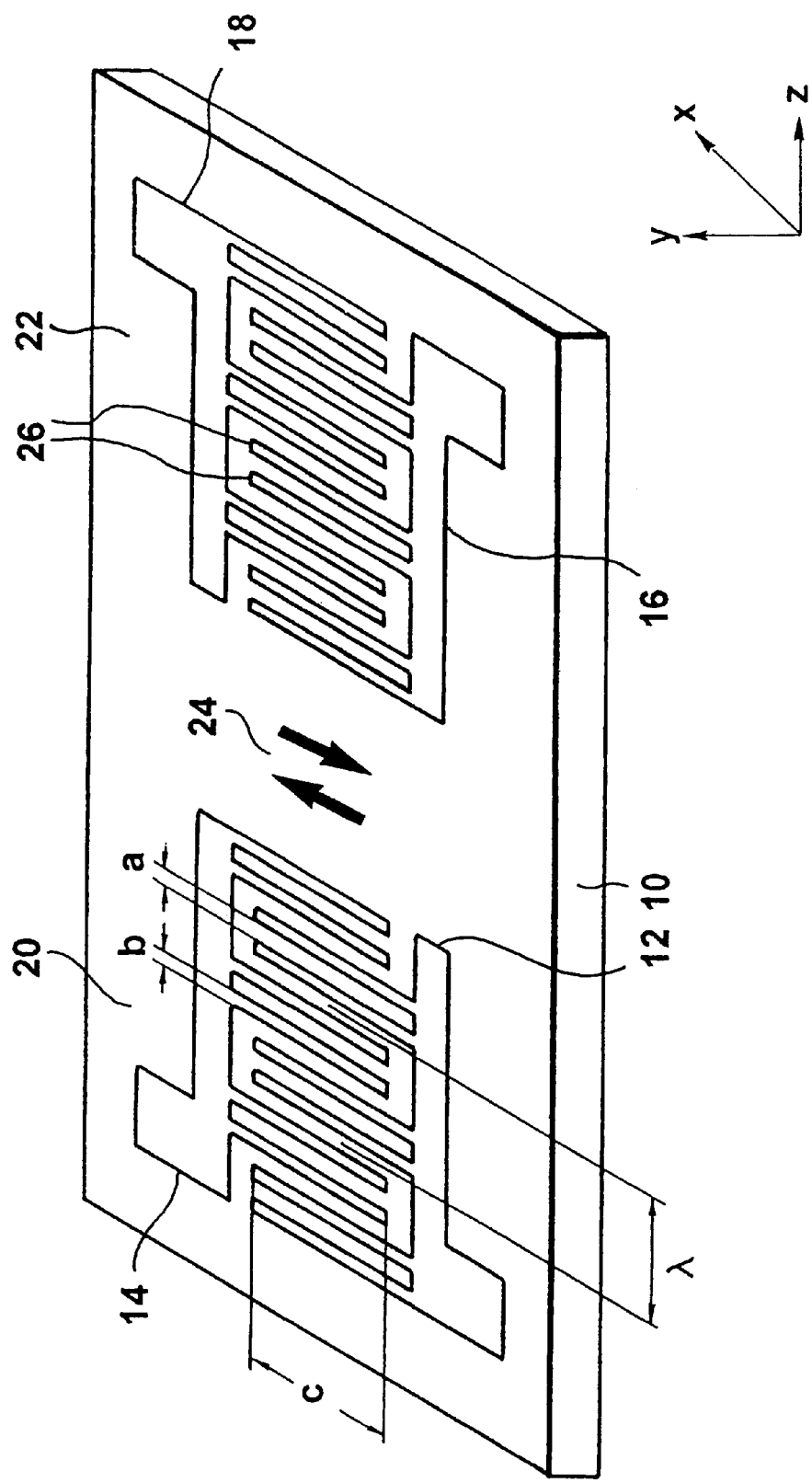

In the following a general description of the surface-wave component shown in FIG. 1 will be given in brief. A piezoelectric substrate 10, e.g. a y-rotated quartz crystal, has comb-shaped electrodes 12, 14, 16 and 18, in thin-film technology e.g., applied to it. The electrodes 12 and 14 form a first interdigital transducer (IDT) 20, the so-called transmitting interdigital transducer (transmitting IDT), while the electrodes 16 and 18 form a second interdigital transducer 22, the so-called receiving interdigital transducer (receiving IDT). The substrate can consist of any sort of piezoelectric material which is suitable for the excitation of shear waves. Preferably a y-rotated quartz crystal with a quartz crystal cut between 35° and 40° is used.

When a high-frequency alternating voltage is applied to the transmitting IDT 20, electroacoustic waves, represented schematically in FIG. 1 by the arrows with the reference numeral 24, are generated because of the piezoelectricity of the material of the substrate 10. The distance between the fingers of the interdigital transducers imposes a wavelength λ, the excitation frequency $f=\upsilon/\lambda$ being determined by the material-dependent propagation speed $\upsilon$ of the wave.

As is shown in FIG. 1, so-called double-finger transducers (also called double-split transducers) are used to suppress the reflections at the fingers. In these transducers two fingers of an electrode are arranged next to each other in each case and form a finger quartet with two fingers of the other electrode of the interdigital transducer, which are arranged next to the finger pair of the first electrode. A finger pair of the electrode 16 is indicated by the reference numeral 26. As is also shown in FIG. 1, the width of a finger is indicated by b and the distance between two neighbouring fingers is indicated by a. The length of the over-lapping region of the fingers of two facing electrodes is indicated by c. The wavelength λ, as is shown in FIG. 1, is equal to the length of a finger quartet, i.e. four times the width of a finger plus four times the distance between neighbouring fingers.

With a suitable choice of substrate material and surface orientation, a wave excited by the transmitting IDT propagates along this surface and generates a high-frequency alternating voltage, which can be electronically evaluated, in the receiving IDT. Changes in the physical boundary conditions along the component surface due to liquids or coatings affect the propagation speed, i.e. the frequency, and the amplitude of the waves and can be used as a sensor effect.

How the surface-wave component described above can be used as a liquid sensor with a high sensitivity to liquid properties and small design-induced disturbances will be explained in the following.

The relative frequency change of a surface wave as a measurement effect in surface-shear-wave sensors when the sensor surface is loaded with a Newtonian liquid is given by $$\frac{\Delta f}{f} = c \cdot \sqrt{\frac{\eta \cdot \rho}{f}}$$

where c is a proportionality constant, η is the viscosity of the Newtonian liquid, is the density of the Newtonian liquid and f is the frequency. The relative frequency change as a measurement effect thus decreases with increasing frequency, so that components with a lower frequency have a higher sensitivity to viscosity changes. The penetration depth of the wave into the liquid is proportional to $\sqrt{(2\cdot\eta/\rho\cdot f)}$ and increases with falling frequency, so that boundary surface effects play a smaller role at low frequencies. Apart from an increase in the effective measurement volume, a low frequency thus leads to improved sensor properties. Thus frequencies below 100 MHz are preferably used for surface-wave liquid sensors.

In addition to the surface shear waves (SSWs), bulk shear waves, e.g. the so-called 'surface skimming bulk waves' (SSBWs) can also be excited in y-rotated quartz crystals, as mentioned above. The frequencies of the SSWs and the SSBWs lie very close to one another.

Analogously to an optical grating, a frequency bandwidth is determined by the number of finger quartets of the interdigital transducers. When these sensors are manufactured normally, with aluminum as the electrode material, and low frequencies are used, as are necessary for the measurement of the viscosity, the frequency bands of the SSW and the SSBW overlap, both modes being excited simultaneously. Due to the sensor effect, the speed and the attenuation of the SSW (surface shear wave) change. The speed and the attenuation of the SSBWs do not change, however, or only very slightly. The interference of the various shear waves thus depends on the sensor effect and disturbs the evaluation considerably. If a surface-wave component of the type described above is to be used as a liquid sensor, the simultaneous excitation of the surface shear wave and the bulk shear waves must be prevented.

In order to prevent an interference of the type cited above, it must be arranged that the SSW and the SSBWs have different frequencies. The boundary conditions on the boundary surface between the quartz substrate and the metallization of the electrodes are determined by the physical properties of the metallization of the IDTs. By changing the physical properties of the metallization of the IDTs it is thus possible e.g. to lower the speed υ and thus the frequency f of the SSW. The excitation frequency of the SSBWs is not affected by such a modification in the physical properties of the metallization, or at least is affected much more weakly than the frequency of the SSW. By suitably adjusting the bandwidth of the SSW via the number of fingers of the interdigital transducers and by increasing the frequency separation of the SSW from the SSBWs by means of a suitable metallization, the excitation band of the SSBWs can be made to lie outside the frequency band of the SSW. As a result, an excitation of the SSBWs is prevented and an interference between the SSW and the SSBWs no longer occurs.

The relative frequency change of the SSW due to the electrode material is given approximately by the following formula:

$$\left(\frac{\Delta f}{f}\right)_m = \frac{(2\cdot\pi)^2}{2} \cdot \left(\frac{\gamma \cdot h \cdot \rho_m}{\lambda}\right)^2 \cdot \frac{1}{c_{66}^2} \cdot [v_c^2 - v_m^2]^2$$

where γ is the metallization ratio (=b/(a+b), width/(width+distance) of the electrodes), $\rho_m$ is the density of the metallization, h is the layer height of the metallization, is the wavelength, $c_{66}$ is the shear rigidity of quartz as a function of the cutting angle of the substrate, $\upsilon_m$ is the acoustic speed of the metallization and $V_c$ is the speed of the SSBWs as a function of the cutting angle of the substrate.

The relative bandwidth $(\Delta f/f)_N$ within which the SSW can be excited is determined by the number of finger quartets N and can be shown to be given by $(\Delta f/f)_N=2/N$.

In order that the interference between the SSW and the SSBWs can be prevented, the following relationship must hold:

$$\left(\frac{\Delta f}{f}\right)_N < \left(\frac{\Delta f}{f}\right)_m$$

It follows that $N>2\cdot(f/\Delta f)_m$.

With aluminum, commonly used in filter technology as the electrode material, the small mass per unit area $\rho_m\cdot h\cdot\gamma$ and the small difference in the acoustic speeds between aluminum ($\upsilon_m$) and the SSBWs ($\upsilon_c$) results in a figure of the order of $10^4$ for the number of finger quartets at a frequency of about 50 MHz for a y-rotated quartz crystal cut of 36°. A filter with such a number of fingers is not suitable for technical realization.

For low frequencies, e.g. under 100 MHz, therefore, in accordance with the above equation, a metallization with a high mass per unit area and low acoustic speed must be used. Suitable materials for the metallization of the electrodes of the interdigital transducers are e.g. gold, platinum or copper. For example, for gold with a layer height h of 350 nm the result, at 65 MHz for a y-rotated quartz cut of 36°, is a minimum number of 75 finger quartets.

Thus it is possible, according to the present invention, to implement a surface-wave liquid sensor with a high sensitivity to liquid properties and small disturbances due to an interference between the surface shear wave and the bulk shear waves.

A further problem in the use of surface-wave components as liquid sensors, which can be solved by an advantageous embodiment of the present invention, is the triple transit echo (TTE) and the electromagnetic crosstalk (EM).

An electroacoustic wave propagating in the region of the receiving interdigital transducer creates in the fingers, or in the busbars of the fingers, via the electric connected load impedance, a potential difference, which in turn generates a surface wave which propagates back in the direction of the transmitting interdigital transducer where it, too, via the generator impedance, generates a wave which propagates back in the direction of the receiver. The twice reflected wave arriving at the receiving interdigital transducer as a result of these effects has covered the measurement path three times and has therefore undergone a phase shift which is three times that of the unreflected wave. This effect is called triple transit echo (TTE). The same results in a frequency-dependent constructive or destructive interference between the direct measurement signal and the twice reflected signal. This causes a frequency-dependent ripple in the transmission behaviour of the surface-wave component, the amplitude of the ripple depending on the insertion loss (IL) of the component and the TTE suppression. In the evaluation of the sensor effect created by a liquid on the surface shear wave the TTE appears as a disturbance. The measurement error produced depends on the TTE suppression, the insertion loss and the size of the measurement effect.

It is obvious that with increasing insertion loss IL the TTE suppression increases. The relationship is given approximately by the expression: TTE[dB]=2·IL[dB]+12 dB. For sensor applications it is thus advantageous to use surface-wave components with high insertion losses from the transmitting IDT to the receiving IDT so as to keep the influence of the TTE as small as possible. Preferably, losses >10 dB, better still >15 dB, are suitable.

In addition to the TTE, the direct electromagnetic crosstalk between the transmitting IDT and the receiving IDT interferes at the receiving interdigital transducer with the signal of the surface wave and appears in the form of a frequency-dependent ripple as a disturbance in the measurement effect. The amplitude of this ripple depends on the amplitude ratio between the electromagnetic crosstalk EM and the insertion loss IL. The smaller this ratio is, the smaller is the influence of the crosstalk on the measurement result. The electromagnetic crosstalk depends on the construction of the surface-wave component. In practice an attenuation of the electromagnetic crosstalk EM in the range from 50 to 80 dB can be achieved. To keep the influence of the EM small, the insertion loss IL must therefore be kept small, i.e. a large amplitude of the surface wave must be guaranteed.

As is obvious from the foregoing, a conflict exists between the high insertion loss required to suppress the TTE and the low insertion loss needed to minimise the effect of the electromagnetic crosstalk. To achieve a balance between the two effects, the following equation must be satisfied:

EM[dB]=IL[dB]+TTE[dB]=3·IL[dB]+12 dB

For the insertion loss the result is thus:

IL[dB]=(EM[dB]−12 dB)/3

Depending on the suppression of the electromagnetic crosstalk which can be achieved for a particular surface-wave component, this results in a range from 10 dB to 30 dB, preferably from 15 dB to 25 dB, for the insertion loss for surface-wave sensors.

The insertion loss of surface-shear-wave components depends on the quartz crystal cut of the substrate employed, on $(\Delta f/f)_m$, on the number and the overlap length c of the fingers of the IDTs (see FIG. 1) and on an electrical matching to the impedance of the connected measurement device. These parameters must be taken into account when designing the surface-wave component in order to obtain a suitable insertion loss which meets the above requirements.

In the following exact parameters suitable for the realization of a surface-wave liquid sensor according to the present invention will be given in the light of a concrete embodiment. A y-rotated quartz crystal with a quartz crystal cut of 36° is employed as the substrate. Gold having a layer height h of 350 mm is used as the metallization for the electrodes of the interdigital transducers. The metallization ratio γ, i.e. the ratio b/(b+a), is 0.5, i.e. 50%. At an excitation frequency f of 65.6 MHz the resulting wavelength λ is 76 μm. The number of finger quartets for a so-called 'double-split' transducer is 90. The finger overlap c is 25 λ. The surface-wave filter dimensioned in this way has an insertion loss of 20 dB.

The present invention therefore provides surface-wave liquid sensors which can be used for the measurement of physical liquid properties, such as the density, the viscosity, the shear rigidity, the dielectric constant, the conductivity, etc., where the effect of changes in the propagation time and attenuation of surface shear waves in a surface-wave component dimensioned according to the present invention is evaluated. The design of the sensors is here optimized in such a way that the influence on the measurement quantities of reflections and interferences with other waveforms is minimized.

What is claimed is:

1. A liquid sensor comprising comb-shaped electrodes, applied to a piezoelectric substrate, as interdigital transducers for generating an electroacoustic wave from a transmitting transducer to a receiving transducer, where the transmitting transducer generates a surface shear wave and a bulk shear wave, wherein:

the number of finger pairs of the interdigital transducers and the material out of which the electrodes are made are so chosen that the surface shear wave generated by the transmitting transducer and the bulk shear wave generated by the transducer have different frequencies, for the interdigital transducers, two fingers of an electrode are arranged next to one another in each case and form a pair, a pair of one electrode forming a finger quartet with a neighboring pair of the second electrode, and the number N of finger quartets is calculated according to the following formulae:

$$\left(\frac{\Delta f}{f}\right)_m = \frac{(2 \cdot \pi)^2}{2} \cdot \left(\frac{\gamma \cdot h \cdot \rho_m}{\lambda}\right) \cdot \frac{1}{c_{66}^2} \cdot [v_c^2 - v_m^2]$$

$$\left(\frac{\Delta f}{f}\right)_N = \left(\frac{\Delta f}{f}\right)_m \text{ and } N > 2 \cdot (f/\Delta f)_m$$

where Δf is the frequency difference between the surface shear wave and the bulk shear wave, f is the excitation frequency of the transmitting transducer, γ is the ratio width(width+distance) of the electrode fingers, h is the height of the electrodes, $\rho_m$ is the density of the electrode material, λ is the wavelength, $c_{66}$ is the shear rigidity coefficient of the substrate material as a function of the cutting angle, $v_c$ is the speed of the bulk shear wave as a function of the cutting angle, and $v_m$ is the acoustic propagation speed in the electrode material.

2. The liquid sensor according to claim 1, wherein the selected electrode material has a small acoustic propagation speed.

3. The liquid sensor according to claim 1, wherein the selected electrode material has a high mass per unit area.

4. The liquid sensor according to claim 1, wherein the substrate is a y-rotated quartz crystal with a quartz crystal cut between 35° and 40°.

5. The liquid sensor according to claim 1, wherein the electrodes are made of gold, platinum or copper.

6. The liquid sensor according to claim 1, wherein the quartz crystal cut of the piezoelectric cubstrate, the material of the electrodes and the number and the overlapping of the finger pairs of the interdigital transducers are so chosen that the insertion loss of an electroacoustic wave between the transmiting transducer and the receiving transducer is set to between 10 and 30 db, preferably between 15 and 25 db.

7. The liquid sensor according to claim 6, wherein
the insertion loss which is to be set is calculated as a function of the electromagnetic crosstalk between the transmitting transducer and the receiving transducer as follows:

$$IL[dB]=(EM[dB]-12\ dB)/3.$$

8. The lilquid sensor according to claim 1, wherein the excitation frequency of the transmitting transducer lies below 100 MHz.

* * * * *